US009945838B2

(12) United States Patent
Doyle (10) Patent No.: US 9,945,838 B2
(45) Date of Patent: Apr. 17, 2018

(54) EXTRACORPOREAL CIRCUIT BLOOD CHAMBER HAVING AN INTEGRATED DEAERATION DEVICE

(71) Applicant: Fresenius Medical Care Holdings, Inc., Waltham, MA (US)

(72) Inventor: Matthew Doyle, Concord, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 114 days.

(21) Appl. No.: 14/972,769

(22) Filed: Dec. 17, 2015

(65) Prior Publication Data

US 2017/0173243 A1 Jun. 22, 2017

(51) Int. Cl.
*G01N 33/48* (2006.01)
*G01N 33/49* (2006.01)
*A61M 1/36* (2006.01)

(52) U.S. Cl.
CPC ............. *G01N 33/49* (2013.01); *A61M 1/361* (2014.02); *A61M 1/3627* (2013.01); *A61M 2205/3306* (2013.01); *A61M 2205/3584* (2013.01); *A61M 2205/502* (2013.01); *A61M 2205/52* (2013.01); *A61M 2205/702* (2013.01); *A61M 2230/207* (2013.01)

(58) Field of Classification Search
CPC ............. A61M 1/1621; A61M 1/3627; A61M 2205/3306; A61M 2205/3584; A61M 2205/502; A61M 2205/52; A61M 2205/702; A61M 2230/207; G01N 33/49
USPC .......................................................... 356/41
See application file for complete search history.

(56) References Cited

U.S. PATENT DOCUMENTS

| | | | |
|---|---|---|---|
| 3,946,731 A | 3/1976 | Lichtenstein | |
| 3,982,538 A | 9/1976 | Sharpe | |
| 3,985,135 A | 10/1976 | Carpenter et al. | |
| 3,996,027 A | 12/1976 | Schnell et al. | |
| 4,014,206 A | 3/1977 | Taylor | |
| 4,026,669 A | 5/1977 | Leonard et al. | |

(Continued)

FOREIGN PATENT DOCUMENTS

| | | |
|---|---|---|
| DE | 102005001779 | 9/2006 |
| EP | 0327136 | 8/1989 |

(Continued)

OTHER PUBLICATIONS

Acu-men, Acute Dialysis Machine Operating Instructions, Software Version 1.0, Fresenius MY acu-men, 1105.96 (OP), 146 pages.

(Continued)

*Primary Examiner* — Hina F Ayub
(74) *Attorney, Agent, or Firm* — Fish & Richardson P.C.

(57) ABSTRACT

A deaeration device includes a vent structure with a porous material capable of swelling when moistened such that the vent structure can inhibit liquid from escaping while allowing for the removal of gases from liquids. The deaeration device is integrated into a blood chamber of an extracorporeal circuit. The blood chamber may further include sensor components for actively performing measurements on the blood while the deaeration device passively removes air from the blood. In an embodiment, the blood chamber may be an optical blood chamber including an optical measurement sensor that performs measurements used in a determination of a hematocrit level in the blood.

24 Claims, 5 Drawing Sheets

(56) References Cited

U.S. PATENT DOCUMENTS

| | | | |
|---|---|---|---|
| 4,061,031 A | 12/1977 | Grimsrud | |
| 4,137,160 A | 1/1979 | Ebling et al. | |
| 4,187,057 A | 2/1980 | Xanthopoulos | |
| 4,231,370 A | 11/1980 | Mroz et al. | |
| 4,326,518 A * | 4/1982 | Williams | A61M 39/288 251/7 |
| 4,370,983 A | 2/1983 | Lichtenstein | |
| 4,459,139 A | 7/1984 | vonReis et al. | |
| 4,488,961 A | 12/1984 | Spencer | |
| 4,530,759 A | 7/1985 | Schal | |
| 4,572,724 A | 2/1986 | Rosenberg et al. | |
| 4,590,227 A | 5/1986 | Nakamura et al. | |
| 4,643,713 A | 2/1987 | Viitala | |
| 4,662,906 A | 5/1987 | Matkovich et al. | |
| 4,695,385 A | 9/1987 | Boag | |
| 4,702,675 A | 10/1987 | Aldrovandi et al. | |
| 4,702,829 A | 10/1987 | Polaschegg et al. | |
| 4,888,004 A | 12/1989 | Williamson | |
| 4,997,464 A | 3/1991 | Kopf | |
| 5,061,236 A | 10/1991 | Sutherland et al. | |
| 5,330,425 A | 7/1994 | Utterberg | |
| 5,372,136 A | 12/1994 | Steuer et al. | |
| 5,425,173 A | 6/1995 | Moss et al. | |
| 5,441,636 A | 8/1995 | Chevallet et al. | |
| 5,460,490 A | 10/1995 | Carr et al. | |
| 5,498,338 A | 3/1996 | Kruger et al. | |
| 5,540,265 A | 7/1996 | Polaschegg et al. | |
| 5,578,070 A | 11/1996 | Utterberg | |
| 5,591,344 A | 1/1997 | Kenley et al. | |
| 5,614,677 A | 3/1997 | Wamsiedler et al. | |
| 5,628,908 A | 5/1997 | Kamen et al. | |
| 5,643,205 A | 7/1997 | Utterberg | |
| 5,651,893 A | 7/1997 | Kenley et al. | |
| 5,674,390 A | 10/1997 | Matthews et al. | |
| 5,674,404 A | 10/1997 | Kenley et al. | |
| 5,690,831 A | 11/1997 | Kenley et al. | |
| 5,711,883 A | 1/1998 | Folden et al. | |
| 5,714,060 A | 2/1998 | Kenley et al. | |
| 5,725,776 A | 3/1998 | Kenley et al. | |
| 5,788,671 A | 8/1998 | Johnson | |
| 5,849,065 A | 12/1998 | Wojke | |
| 5,863,421 A | 1/1999 | Peter | |
| 5,928,177 A | 7/1999 | Brugger et al. | |
| 5,938,634 A | 8/1999 | Packard | |
| 5,989,423 A | 11/1999 | Kamen et al. | |
| 6,179,801 B1 | 1/2001 | Holmes et al. | |
| 6,196,987 B1 | 3/2001 | Holmes et al. | |
| 6,200,287 B1 | 3/2001 | Keller et al. | |
| 6,231,537 B1 | 5/2001 | Holmes et al. | |
| 6,234,989 B1 | 5/2001 | Brierton et al. | |
| 6,280,406 B1 | 8/2001 | Dolecek et al. | |
| 6,336,916 B1 | 1/2002 | Bormann et al. | |
| 6,337,049 B1 | 1/2002 | Tamari | |
| 6,361,518 B1 | 3/2002 | Brierton et al. | |
| 6,383,158 B1 | 5/2002 | Utterberg et al. | |
| 6,409,696 B1 | 6/2002 | Toavs et al. | |
| 6,497,674 B1 | 12/2002 | Steele et al. | |
| 6,497,676 B1 | 12/2002 | Childers et al. | |
| 6,514,225 B1 | 2/2003 | Utterberg et al. | |
| 6,536,278 B1 | 3/2003 | Scagliarini | |
| 6,695,803 B1 | 2/2004 | Robinson et al. | |
| 6,725,726 B1 | 4/2004 | Adolfs et al. | |
| 6,730,055 B2 | 5/2004 | Bainbridge et al. | |
| 6,743,201 B1 | 6/2004 | Diinig et al. | |
| 6,755,801 B2 | 6/2004 | Utterberg et al. | |
| 6,764,460 B2 | 7/2004 | Dolecek et al. | |
| 6,790,195 B2 | 9/2004 | Steele et al. | |
| 6,852,090 B2 | 2/2005 | Burbank et al. | |
| 6,887,214 B1 | 5/2005 | Levin et al. | |
| 6,979,309 B2 | 12/2005 | Burbank et al. | |
| 7,021,148 B2 | 4/2006 | Kuhn | |
| 7,115,107 B2 | 10/2006 | Delnevo et al. | |
| 7,238,164 B2 | 7/2007 | Childers et al. | |
| 7,476,209 B2 | 1/2009 | Gara et al. | |
| 7,517,387 B2 | 4/2009 | Chevallet et al. | |
| 7,603,907 B2 | 10/2009 | Reiter et al. | |
| 7,621,983 B2 | 11/2009 | Neri | |
| 7,871,391 B2 | 1/2011 | Folden et al. | |
| 7,892,331 B2 | 2/2011 | Childers et al. | |
| 7,892,332 B2 | 2/2011 | Prisco et al. | |
| 7,905,853 B2 | 3/2011 | Chapman et al. | |
| 7,938,967 B2 | 5/2011 | Folden et al. | |
| 8,038,886 B2 | 10/2011 | Folden et al. | |
| 8,110,104 B2 | 2/2012 | Crnkovich et al. | |
| 8,130,369 B2 | 3/2012 | Barrett et al. | |
| 8,187,466 B2 | 5/2012 | Folden et al. | |
| 8,287,739 B2 | 10/2012 | Barrett et al. | |
| 8,333,724 B2 | 12/2012 | Barrett et al. | |
| 8,425,780 B2 | 4/2013 | Beiriger | |
| 8,506,684 B2 | 10/2013 | Weaver et al. | |
| 8,663,463 B2 | 3/2014 | Weaver et al. | |
| 9,173,998 B2 | 11/2015 | Barrett et al. | |
| 9,194,792 B2 | 11/2015 | Barrett et al. | |
| 2002/0014462 A1 | 2/2002 | Muller | |
| 2002/0072718 A1 | 6/2002 | Brugger et al. | |
| 2002/0179527 A1 | 12/2002 | Yao | |
| 2004/0019312 A1 | 1/2004 | Childers et al. | |
| 2004/0238416 A1 | 12/2004 | Burbank et al. | |
| 2005/0054968 A1 | 3/2005 | Giannella | |
| 2005/0126998 A1 | 6/2005 | Childers | |
| 2005/0131332 A1 | 6/2005 | Kelly et al. | |
| 2005/0132826 A1 | 6/2005 | Teugels | |
| 2005/0230292 A1 | 10/2005 | Beden et al. | |
| 2007/0078369 A1 | 4/2007 | Tamari | |
| 2007/0086924 A1 | 4/2007 | Moses | |
| 2007/0106198 A1 | 5/2007 | Folden et al. | |
| 2007/0112297 A1 | 5/2007 | Plahey et al. | |
| 2007/0193940 A1 | 8/2007 | Duchamp et al. | |
| 2007/0269340 A1 | 11/2007 | Dannenmaier et al. | |
| 2008/0275364 A1 | 11/2008 | Conway et al. | |
| 2009/0012449 A1 | 1/2009 | Lee et al. | |
| 2009/0071911 A1 | 3/2009 | Folden et al. | |
| 2009/0084721 A1 | 4/2009 | Yardimci et al. | |
| 2009/0101576 A1 | 4/2009 | Rohde et al. | |
| 2009/0216211 A1 | 8/2009 | Beden et al. | |
| 2009/0320684 A1 | 12/2009 | Weaver | |
| 2010/0133189 A1 | 6/2010 | Maierhofer et al. | |
| 2010/0206784 A1 | 8/2010 | Weaver et al. | |
| 2010/0222735 A1 | 9/2010 | Plahey et al. | |
| 2010/0292627 A1 | 11/2010 | Caleffi et al. | |
| 2011/0120946 A1 | 5/2011 | Levin et al. | |
| 2012/0059303 A1 * | 3/2012 | Barrett | A61B 5/14557 604/5.01 |
| 2013/0237897 A1 | 9/2013 | Crnkovich et al. | |
| 2014/0052044 A1 | 2/2014 | Crnkovich et al. | |

FOREIGN PATENT DOCUMENTS

| | | |
|---|---|---|
| EP | 0458041 | 11/1991 |
| EP | 0728509 | 8/1996 |
| EP | 0887100 | 12/1998 |
| EP | 1529545 | 5/2005 |
| EP | 1547630 | 6/2005 |
| EP | 1728526 | 3/2008 |
| EP | 1894587 | 3/2008 |
| EP | 2226087 | 9/2010 |
| JP | 2003-180834 | 7/2003 |
| JP | 2005-530543 | 10/2005 |
| WO | 96/40322 | 12/1996 |
| WO | 01/08722 | 2/2001 |
| WO | 01/50949 | 7/2001 |
| WO | 01/64312 | 9/2001 |
| WO | 02/26286 | 4/2002 |
| WO | 2004/000391 | 12/2003 |
| WO | 2005/044340 | 5/2005 |
| WO | 2005/044341 | 5/2005 |
| WO | 2005/065745 | 7/2005 |
| WO | 2005/077490 | 8/2005 |

(56) References Cited

FOREIGN PATENT DOCUMENTS

| WO | 2007/050211 | 5/2007 |
|----|-------------|--------|
| WO | 2008/002370 | 1/2008 |

OTHER PUBLICATIONS

Communication Pursuant to Article 94(3) EPC, EP 10154030. 0, Jul. 2, 2010, 4 pages.
European Search Report, EP 10154030, Jun. 21, 2010, 3 pages.
Gambro®, "DEHP-Free Cartridge Blood Sets", © Nov. 2004, Gambro, Inc, Lakewood, CO, 4 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™, Anticipating Critical Care needs and taking our innovative response . . . to new heights", © 2004, Gambro Inc., Lakewood, CO, 8 pp.
Gambro®, Prisma® HF 1000, "For Increased Filtration Capacity", © Aug. 2001, Gambro Renal Products, Inc., Lakewood, CO, 2 pp.
International Search Report and Written Opinion; PCT/US06/36802; dated May 8, 2008, 8 pp.
International Search Report and Written Opinion; PCT/US2008/076830; dated Dec. 29, 2008, 19 pp.
Manns, Markus et al., "The acu-men: A new device for continuous renal replacement therapy in acute renal failure," Kidney International, vol. 54, pp. 268-274, 1998.

\* cited by examiner

EXTRACORPOREAL CIRCUIT BLOOD CHAMBER HAVING AN INTEGRATED DEAERATION DEVICE

TECHNICAL FIELD

This application generally relates to dialysis systems and, more particularly, to a deaeration system for removing gases from a blood chamber of an extracorporeal circuit, such as a hemodialysis blood circuit.

BACKGROUND

Hemodialysis removes toxic substances and metabolic waste from the bloodstream using an extracorporeal circuit with components designed to perform ultrafiltration and diffusion on the blood. Before the blood is returned to the body, air bubbles are removed from the blood to inhibit embolisms. The process of removing air is typically accomplished through use of a venous drip chamber, which is located downstream of the blood outlet of a dialyzer and directly upstream of the venous blood return of the patient. A level detector is used to ensure that an associated clamp closes when the venous drip chamber blood level drops below a certain level to prevent air from entering into the patient.

Devices are known that provide for air removal through use of a micro-porous membrane and a vent structure associated with the venous drip chamber. Such devices generally involve use of a specialized module for attachment to a specialized blood tubing cassette. Reference is made, for example, to U.S. Pat. Nos. 8,187,466 B2 and 7,938,967 B2, both to Folden et al. and entitled "Safety vent Structure for extracorporeal circuit" and U.S. Pat. No. 8,038,886 B2 to Folden et al., entitled "Medical hemodialysis container including a self sealing vent," which are all incorporated herein by reference and which disclose air-release devices that include a porous material capable of swelling when moistened such that the vent structure can inhibit liquid from escaping the air-release device during use. For discussion of other air-release devices used in extracorporeal fluid circuits, reference is also made to U.S. Pat. No. 8,506,684 B2 to Weaver et al., entitled "Gas release devices for extracorporeal fluid circuits and related methods" and U.S. Pat. No. 8,663,463 to Weaver et al., entitled "Extracorporeal fluid circuit and related components," which are incorporated herein by reference.

Accordingly, it would be desirable to provide a deaeration device for an extracorporeal circuit that may be advantageously integrated into and operate with existing hemodialysis machines and/or associated devices, including devices performing measurements on blood in the extracorporeal circuit.

SUMMARY

According to the system described herein, an extracorporeal blood circuit device includes a blood chamber and a deaeration device integrated with the blood chamber for removing air from blood flowing into the blood chamber. A sensor is provided for measuring a blood constituent level, and in which the sensor performs measurements on blood in the blood chamber while the deaeration device removes air from the blood in the blood chamber. The deaeration device may further include a vent assembly integrated with a side of the blood chamber, and the vent assembly may include a micro-porous membrane and a vent structure. The vent structure may include a first porous layer and a second porous layer including a porous material capable of swelling when moistened. The first porous layer may be disposed between the micro-porous membrane and the second porous layer and the first porous layer may be less responsive to the presence of moisture than the second porous layer. The blood chamber may be an optical blood chamber, the sensor may include an optical measurement sensor, and the blood constituent level measured by the sensor may enable determination of a hematocrit level and/or an oxygen saturation level in the blood. The deaeration device passively removes air from the blood in the blood chamber while the sensor actively performs measurements on the blood in the blood chamber.

According further to the system described herein, a dialysis system includes a dialyzer and an extracorporeal blood circuit device disposed adjacent to the dialyzer. The extracorporeal blood circuit device includes a blood chamber and a deaeration device integrated with the blood chamber for removing air from blood flowing into the blood chamber. The extracorporeal blood circuit device may further include a sensor for measuring a blood constituent level, in which the sensor performs measurements on blood in the blood chamber while the deaeration device removes air from the blood in the blood chamber. In various embodiments, the blood chamber is configured as an S-shaped in tubing coupled to the dialyzer, the extracorporeal blood circuit device is coupled to an outlet of the dialyzer and/or the extracorporeal blood circuit device is coupled to an inlet of the dialyzer. The extracorporeal blood circuit device may be a first extracorporeal blood circuit device having a first blood chamber and a first deaeration device, and the dialysis system may further comprise a second extracorporeal blood circuit device comprising a second blood chamber and a second deaeration device integrated with the second blood chamber for removing air from blood flowing into the second blood chamber. The first extracorporeal blood circuit device may be coupled to an outlet of the dialyzer and may further comprise a sensor for measuring a blood constituent level. The sensor performs measurements on blood in the first blood chamber while the deaeration device removes air from the blood in the first blood chamber, and the second extracorporeal blood circuit is coupled to an inlet of the dialyzer. The deaeration device may comprise a vent assembly integrated with a side of the blood chamber. The blood chamber may be an optical blood chamber, the sensor may include an optical measurement sensor, and the blood constituent level measured by the sensor may enable determination of a hematocrit level in the blood.

According further to the system described herein, a method for measuring and deaerating blood in an extracorporeal blood circuit includes coupling a blood chamber with integrated deaeration device to an outlet of a dialyzer. The method further includes passively deaerating blood flowing into the blood chamber from the dialyzer using the integrated deaeration device and actively performing measurements on the blood in the blood chamber using a sensor of the blood chamber. The blood chamber may be an optical blood chamber, the sensor may include an optical measurement sensor, and the blood constituent level measured by the sensor may enable determination of a hematocrit level in the blood.

BRIEF DESCRIPTION OF THE DRAWINGS

Embodiments, advantages, and features of the system described herein are explained with reference to the several figures of the drawings, which are briefly described as follows.

DETAILED DESCRIPTION OF VARIOUS EMBODIMENTS

Figure 1:
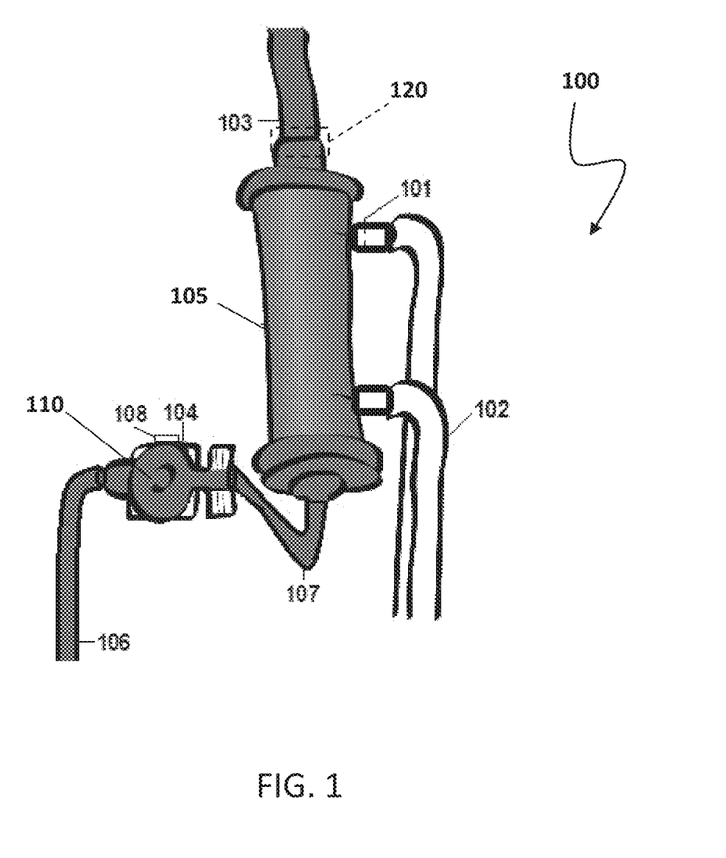
FIG. 1 is a schematic illustration of a portion of an extracorporeal blood circuit including a deaeration device 104 integrated with a blood chamber configured to allow for optical fluid detection according to an embodiment of the system described herein.

FIG. 1 is a schematic illustration of a portion of an extracorporeal blood circuit 100 including a deaeration device 104 integrated with a blood chamber 110 configured to allow for optical fluid detection according to an embodiment of the system described herein. The deaeration device 104 is integrated directly onto a side of the blood chamber 110 and thereby may be in contact with blood while it is flowing into and within the blood chamber. The dialysate circuit comprises an arterial bloodline 103, a dialyzer 105, and a venous bloodline 106. Attached to the extracorporeal circuit are a fresh dialysate line 101 and a spent dialysate line 102. Additionally, the extracorporeal circuit comprises intermediate blood-tubing 107. The intermediate blood tubing 107 and the deaeration device 104 connect to each other along with the dialyzer 105 and venous blood tubing 106 through use of luer-lock connections. It should be appreciated that the system of FIG. 1 demonstrates an example embodiment of the system, and that other possible configurations of the system of the system described herein may be equally or even more suitable, depending on specific requirements. For example, a deaeration device (like the deaeration device 104 and/or a different embodiment of the deaeration device 104) may be connected between arterial bloodline 103 and dialyzer 105 instead of, or in addition to, being connected between the dialyzer 105 and venous bloodline 106. This is shown schematically in the figure as element 120.

In the illustrated embodiment of FIG. 1, blood from the patient travels through associated pressure monitoring systems (not shown) facilitated by an arterial blood pump (not shown) as it traverses the arterial bloodline 103. As blood enters dialyzer 105, it interacts with fresh dialysate supplied by fresh dialysate line 101, and cleansed blood enters into intermediate blood tubing 107. Intermediate blood-tubing 107 allows for deaeration device 104 to be configured in a way that allows for the porous material to be facing upward to allow for maximal diffusion of air. It should be appreciated, however, that one or more deaeration devices (like the deaeration device 104 or a different embodiment of the deaeration device 104) may be connected elsewhere in the extracorporeal circuit, including directly to dialyzer 105, however, such configurations would potentially require relocation of the porous material to maximize air conglomeration and deaeration properties of the blood chamber 110. Conglomerated air exits the blood chamber 110 via a vent assembly 108 of the deaeration device 104, and cleansed/deaerated blood exits the blood chamber 110 and enters venous blood tubing 106. Upon entering venous blood tubing 106, the blood enters into a venous drip chamber (not shown) with associated pressure monitoring systems and is returned to the patient.

Figure 2:
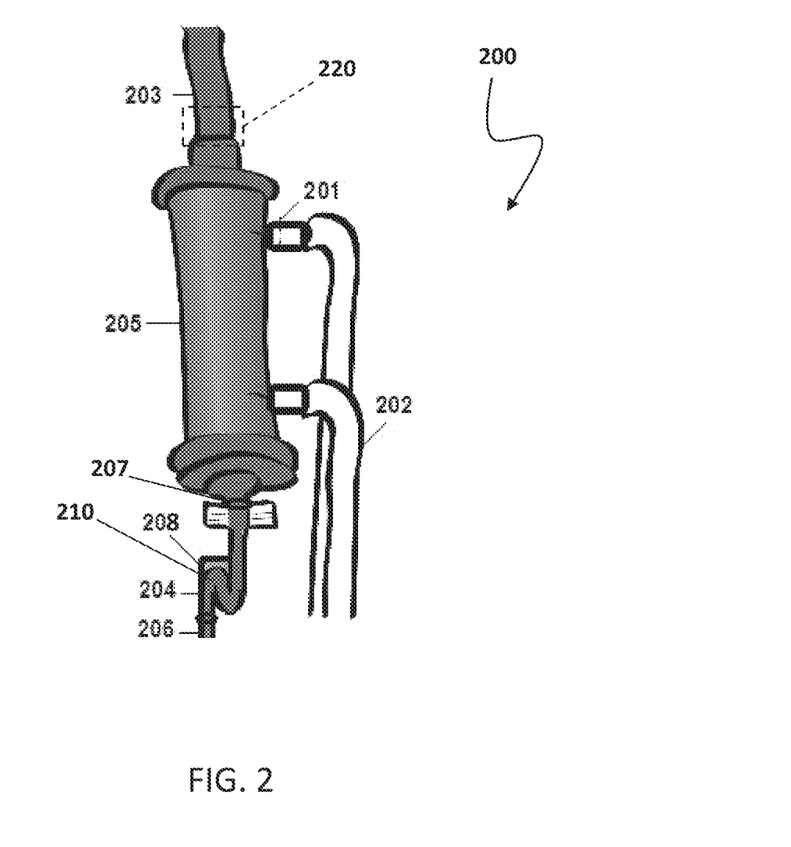
FIG. 2 is a schematic illustration of a portion of an extracorporeal blood circuit with a deaeration device integrated with a blood chamber configured as an S-Bend according to an embodiment of the system described herein.

FIG. 2 is a schematic illustration of a portion of an extracorporeal blood circuit 200 with a deaeration device 204 integrated with a blood chamber 210 configured as an S-Bend according to an embodiment of the system described herein. The extracorporeal circuit 200 comprises an arterial bloodline 203, a dialyzer 205, and a venous bloodline 206. Attached to the extracorporeal circuit 200 are a fresh dialysate line 201 and a spent dialysate line 202. In an embodiment, the deaeration device 204 may connect to the dialyzer 205 and venous blood tubing 206 through use of luer-lock connections. It should be appreciated that while the system of FIG. 2 demonstrates an example embodiment of the system described herein, and that other possible configurations of the system described herein may be equally or even more suitable, depending on specific requirements. For example, a deaeration device (like the deaeration device 204 and/or a different embodiment of the deaeration device 204) may be connected between arterial bloodline 203 and dialyzer 205 instead of, or in addition to, being connected between the dialyzer 205 and the venous bloodline 206. This is shown schematically in the figure as element 220.

Blood from the patient travels through associated pressure monitoring systems (not shown) facilitated by an arterial blood pump (not shown) as it traverses the arterial bloodline 203. As blood enters dialyzer 205, it interacts with fresh dialysate supplied by fresh dialysate line 201, and cleansed blood enters into and cleansed blood enters into intermediate blood tubing 207 (if any) and then into the S-Bend blood chamber 210 with integrated deaeration device 204. The deaeration device 204 is configured in the S-Bend blood chamber 210 so as to provide for air to conglomerate at the top of deaeration device 204 to allow for maximal diffusion of air. Conglomerated air exits the S-bend blood chamber 210 via the deaeration device 204 and through the vent assembly 208 of the deaeration device 204, and cleansed/deaerated blood exits the S-bend blood chamber 210 and enters venous blood tubing 206. Upon entering venous blood tubing 206, the blood enters into a venous drip chamber (not shown) and is returned to the patient.

In an embodiment, the vent assembly may include a micro-porous membrane and a vent structure. Embodiments of the components of the vent assembly may include one or more of the features discussed below. For further details and discussion of vent assembly components, reference is made to U.S. Pat. Nos. 8,187,466 and 7,938,967, discussed elsewhere herein.

The micro-porous membrane of the deaeration device can have an average pore size of about 0.05 microns to about 0.45 microns. The micro-porous membrane can be held by a plastic ring (e.g., by insert molding, heat welding, ultrasonic welding, adhesive, clamping, etc.) and the assembly can also include an insert for holding the micro-porous membrane adjacent to the vent structure. The micro-porous membrane can be between the vent structure of the blood chamber and the blood-flow region of the blood chamber. In some embodiments, a structure or assembly can include a plastic ring into which the micro-porous membrane is pressfit, wherein the ring surrounds the vent structure and retains the vent structure adjacent to the micro-porous membrane.

The vent structure of the deaeration device can have an average pore size of 15 microns to approximately 45 microns. The vent structure can include a polymer such as polyethylene (e.g., high density polyethylene (HDPE), polypropylene, or polystyrene). The vent structure can include a swelling agent such as carboxymethylcellulose (CMC), methyl-ethyl-cellulose or other similar swelling agents. The vent structure can include a blend of a polymer and a swelling agent. The vent structure can include porous material that is capable of swelling when moistened.

The vent structure can include a first porous layer adjacent to the micro-porous membrane, and a second porous layer adjacent to the first porous layer. The second porous layer can include a porous material that is capable of swelling when moistened. The first porous layer can also include a porous material that is capable of swelling when moistened. The second porous layer can have a greater propensity to swell in the presence of moisture than the first porous layer. The second porous layer can have an average pore size that is greater than an average pore size of the first porous layer. For example, the first porous layer can have an average pore size of about 10 microns, and the second porous layer can have an average pore size of about 30 microns. The second porous layer can include about 5% to about 50% by weight carboxymethylcellulose (e.g., about 10% by weight carboxymethylcellulose). The first porous layer can include 0% to about 10% by weight carboxymethylcellulose (e.g., less than 5% by weight carboxymethylcellulose).

In various embodiments, the blood chamber with integrated deaeration device can be connected to extracorporeal venous blood tubing capable of being used with a dialysis machine (see, e.g., FIG. 1), or can be directly incorporated into the venous tubing to result in the need for only one luer lock connection to connect to the dialyzer (see, e.g., FIG. 2) and/or both of these embodiments may be employed concurrently.

In an embodiment, the deaeration device according to the system described herein may be incorporated into an optical blood chamber, such as such chambers produced by Fresenius Medical Care of Waltham, Mass. Reference is made, for example, to U.S. Pat. No. 8,333,724 B2 to Barrett et al., entitled "Low Flow Optical Blood Chamber" and U.S. Pat. No. 9,194,792 B2 to Barrett et al., entitled "Blood Chamber for an Optical Blood Monitoring System," which are incorporated herein by reference.

Figure 3:
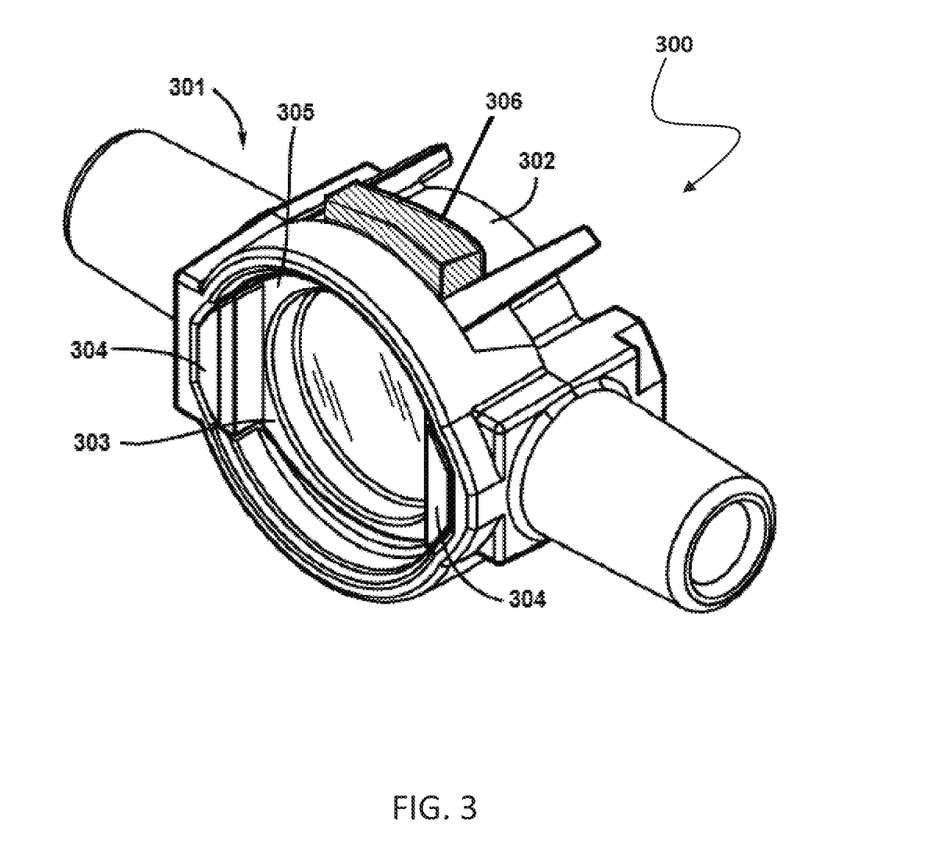
FIG. 3 is a schematic illustration of a blood chamber including an integrated deaeration device according to an embodiment of the system described herein.

FIG. 3 is a schematic illustration of an embodiment 300 of the system described herein showing a blood chamber 301 with an integrated deaeration device 306 according to an embodiment of the system described herein. The blood chamber 301 may be an embodiment of the blood chamber 110 discussed in connection with FIG. 1 and/or may be an embodiment of the blood chamber 120 discussed in connection with FIG. 1. The blood chamber 301 may be an optical blood chamber that includes one or more optical measurement sensors for measuring blood constituent levels, as further discussed elsewhere herein. The blood chamber 301 may be molded from medical grade clear polycarbonate. For specific details of suitable blood chamber requirements, reference is made, for example, to U.S. Pat. Nos. 8,333,724 and 9,194,792, as discussed elsewhere herein.

In an embodiment, the deaeration device is integrated into a blood chamber having a flat, generally elongated internal blood flow cavity and a circular viewing area. The top of the blood chamber includes a vent assembly that may include a micro-porous membrane and a vent structure. A first liquid, such as saline, is passed through the blood chamber which is connected to the blood outlet of a dialyzer and venous blood tubing through two luer-lock connectors. A second liquid, such as blood, is passed through the blood chamber forcing a portion of the first liquid out of an exit port of the blood chamber and forming a liquid-liquid interface between the first and second liquids at the top of the blood chamber. Any gas bubbles contained in the second liquid can be forced out of the micro-porous membrane and the vent structure. The blood chamber may include sensor components or devices for measuring blood constituent levels that function while the integrated deaeration device removes air from the blood.

In an embodiment, the blood chamber 301 may include two molded parts, namely a chamber body 302 and a lens body 303. Connected between the two molded parts is a deaeration device 306 with a vent assembly which allows for deaeration of the blood flowing into the chamber 301. The deaeration device 306 may be configured using one or more porous materials, as further discussed in detail elsewhere herein. The lens body 303 is attached to the chamber body 302 to provide leak-free blood flow chamber 301 and a secure connection of the deaeration device 306. In various embodiments, the lens body 303 may be sonically welded to the chamber body 302 and/or may be secured to the chamber body 302 in other ways, such as using medical grade adhesive.

The lens body 303 may include upstanding pedestals 304 axially disposed along the lens body 303. The pedestals 304 extend outward from a sensor receiving wall 305 on the lens body 303. When the lens body 303 is welded into place in the chamber body 302, the receiving ledge 305 is detented relative to the overall blood chamber 301.

It is noted that the blood chamber 301 may be produced using other designs according to specific requirements and specifications consistent with implementation with an integrated deaeration device according to the system described herein.

The blood chamber 301 may be implemented in connection with a blood monitoring system used during hemodialysis treatment or other treatments involving extracorporeal blood flow. One example is the CRIT-LINE® monitoring system produced by Fresenius Medical Care of Waltham, Mass. The CRIT-LINE® blood monitoring system uses optical techniques to non-invasively measure in real-time the hematocrit and/or the oxygen saturation level of blood flowing through the hemodialysis system. The blood monitoring system measures the blood at a sterile blood chamber attached in-line to the extracorporeal tubing. The blood monitoring system is typically disposed on the arterial side of the dialyzer, but may also be disposed on the venous side of the dialyzer.

In general, blood chambers along with the tube set and dialyzer are replaced for each patient. The blood chamber is intended for a single use. The blood chamber defines an internal blood flow cavity comprising a substantially flat viewing region and two opposing viewing lenses. LED emitters and photodetectors for the optical blood monitor are clipped into place onto the blood chamber over the lenses. Multiple wavelengths of light may be directed through the blood chamber and the patient's blood flowing through the chamber with a photodetector detecting the resulting intensity of each wavelength.

Suitable wavelengths to measure hematocrit are about 810 nm, which is substantially isobestic for red blood cells, and about 1300 nm, which is substantially isobestic for water. A ratiometric technique implemented in the CRIT-LINE® controller, substantially as disclosed in U.S. Pat. No. 5,372,136 to Steuer et al., entitled "System and Method for Non-Invasive Hematocrit Monitoring," and which is incorporated herein by reference, uses this light intensity information to calculate the patient's hematocrit value in real-time. The hematocrit value is a percentage determined by the ratio between (1) the volume of the red blood cells in a given whole blood sample and (2) the overall volume of the blood sample. For further discussion of calculating hematocrit values and other information, and the measurements taken to perform these calculations, reference is made to U.S. Pat. Nos. 8,130,369 B2 and 8,287,739 B2, both to Barrett et al., and entitled "Measuring Hematocrit and Estimating Hemoglobin Values with a Non-Invasive, Optical Blood Monitoring System," which are incorporated herein by reference.

In a clinical setting, the actual percentage change in blood volume occurring during hemodialysis can be determined, in real-time, from the change in the measured hematocrit. Thus, an optical blood monitor is able to non-invasively monitor not only the patient's hematocrit level but also the change in the patient's blood volume in real-time during a hemodialysis treatment session. The ability to monitor real-time change in blood volume helps facilitate safe, effective hemodialysis.

To monitor blood in real time, light emitting diodes (LEDs) and photodetectors for them are mounted on two opposing heads of a sensor clip assembly that fit over the blood chamber. For accuracy of the system, the LEDs and the photodetectors are located in a predetermined position and orientation each time the sensor clip assembly is clipped into place over the blood chamber. The predetermined position and orientation ensures that light traveling from the LEDs to the photodetectors travels through a lens of the blood chamber. The optical monitor may be calibrated for the specific dimensions of the blood chamber and the specific position and orientation of the sensor clip assembly with respect to the blood chamber. For this purpose, the heads of the sensor clips are designed to mate to the blood chamber so that the LEDs and the photodetectors are at known positions and orientations with respect to one another. In various embodiments, the sensor clip assembly may also include processing components and capability to perform one or more of the calculations discussed herein. Reference is made, for example, to U.S. Pat. No. 9,173,988 B2 to Barrett et al., entitled "Sensor Clip Assembly for an Optical Monitoring System," which is incorporated herein by reference, and which discloses a sensor clip assembly for an optical blood monitoring system that includes a circuit board with a microprocessor that is programmed with a ratiometric model to calculate hematocrit and/or oxygen saturation levels of a patient.

In various embodiments, in connection with offloading and/or transmitting or receiving data or other information, the sensor clip assembly may be coupled via a wired connection to a dialysis machine and/or peripheral component, may include an interface for receiving a physical storage unit, e.g. a universal serial bus (USB) memory unit, that may be used to transfer or receive data or information, and/or may include wireless transmission components for transmitting or receiving data or other information wirelessly. For a wireless transmission implementation, the sensor clip assembly may include components for short range wireless transmission technologies, such as WiFi, Bluetooth and/or near field communications (NFC technologies) to communicate with one or more peripheral devices and/or may include network transmission components for transmitting and receiving data and/or other signals wirelessly via a telecommunications network and/or the Internet via one or more remote servers. In connection with such transmission, data may be secured and/or encrypted using appropriate security and encryption protocols according to applicable laws and regulations governing transmission of sensitive data and/or protected medical information.

According to an embodiment of the system described herein, the blood chamber with integrated deaeration device includes devices that can actively perform measurements, such as optical measurements, on the blood flowing through the blood chamber at a same time as the deaeration device passively removes air from the blood. Accordingly, for example, hematocrit and/or oxygen saturation can be measured and calculated at a processor of the blood chamber and/or sensor clip assembly while the deaeration device passively removes air from the blood flowing to the venous bloodlines.

Figure 4A:
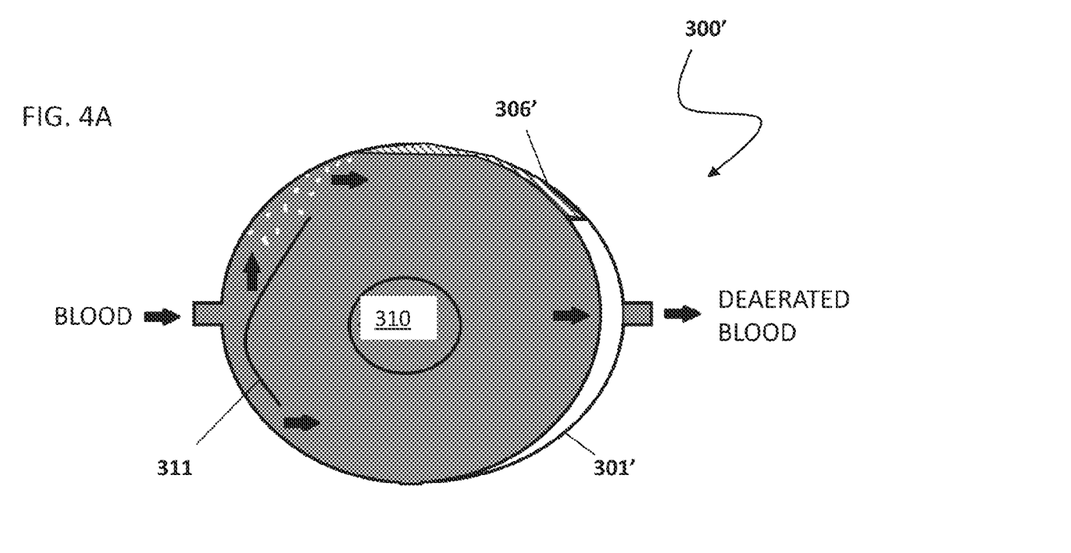
FIGS. 4A and 4B are schematic illustrations showing embodiments for a blood chamber with integrated deaeration device and measuring devices for performing measurements of blood constituent levels in the blood flowing in the blood chamber.
Figure 4B:
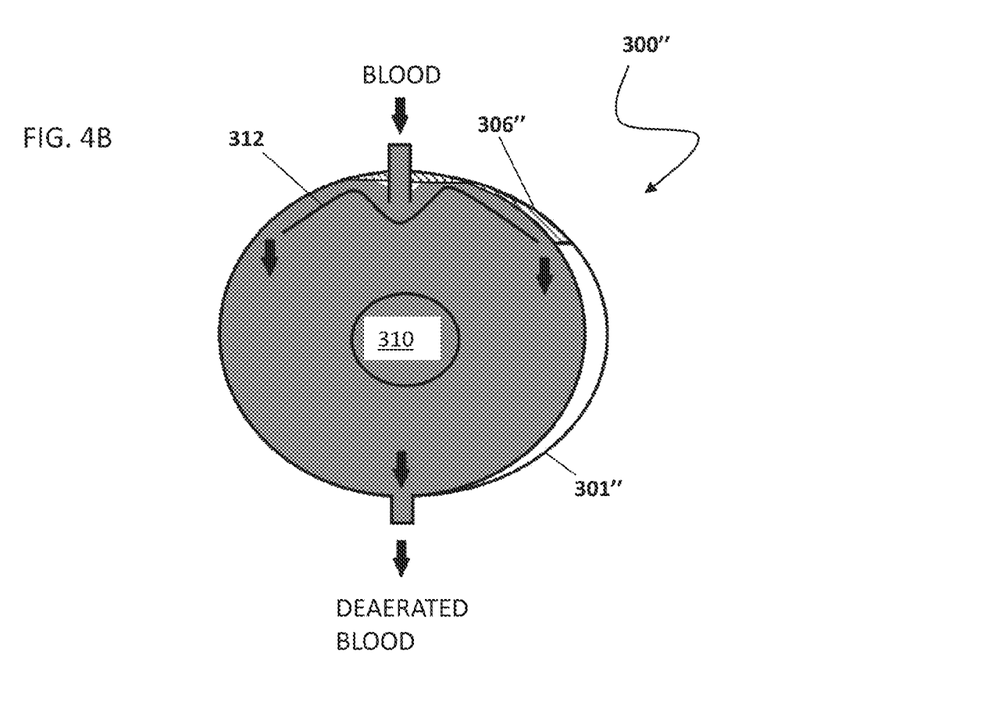

FIGS. 4A and 4B are schematic illustrations showing embodiments 300' and 300" of devices according to the system described herein each including a blood chamber with integrated deaeration device and measuring devices for performing measurements of blood constituent levels in the blood flowing in the blood chamber in which blood flows into the devices 300' and 300' and deaerated blood flows out.

In FIG. 4A, the embodiment 300' shows a blood chamber 301' with integrated deaeration device 306' in one orientation. The blood chamber 301' further includes a region utilized by for one or more sensor components 310 that may be used to measure blood constituent levels as further discussed elsewhere herein. The blood chamber 301' may also include a flow diverter or baffle 311 that may be implemented in connection with diverting blood flow to enable both passive deaeration of the blood in the blood chamber 301' by the integrated deaeration device 306' and measurement of the blood constituent levels in the blood by the one or more sensor components 310.

In FIG. 4B, the embodiment 300" shows a blood chamber 301" with integrated deaeration device 306" in another orientation. The blood chamber 301" further includes a region utilized by for one or more sensor components 310 that may be used to measure blood constituent levels as further discussed elsewhere herein. The blood chamber 301" may also include a flow diverter or baffle 312 that may be implemented in connection with diverting blood flow to enable both passive deaeration of the blood in the blood chamber 301" by the integrated deaeration device 306" and measurement of the blood constituent levels in the blood by the one or more sensor components 310.

Figure 5:
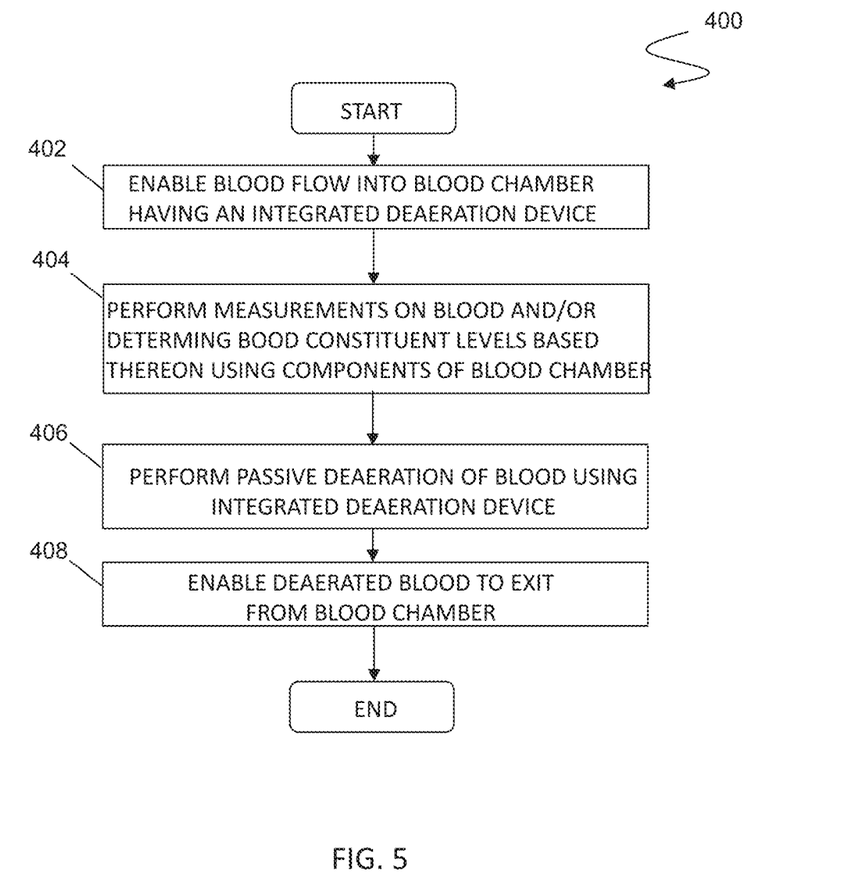
FIG. 5 is a flow diagram showing processing of blood flowing through a blood chamber with integrated deaeration device, such as blood chamber with integrated deaeration device, according to an embodiment of the system described herein.

FIG. 5 is a flow diagram 400 showing processing of blood flowing through a blood chamber with integrated deaeration device, such as blood chamber 301 with integrated deaeration device 306, according to an embodiment of the system described herein. At a step 402, the system operates to enable blood flow into the blood chamber, for example, cleansed blood flowing into the blood chamber from a dialyzer of an extracorporeal circuit during a dialysis treatment. After the step 402, at a step 404 components of the blood chamber perform measurements on the blood, such as optical measurements performed using components of an optical blood chamber, as further discussed elsewhere herein, that may be used in connection with determining blood constituent levels, such as hematocrit levels and/or oxygen saturation levels. It is noted that the determining of the blood constituent levels may be performed by one or more components of the blood chamber, such an onboard processor thereof. After the step 404 (or, at substantially a same time as the step 404), at a step 406 passive deaeration of the blood to remove air is performed via the deaeration device. After the step 406, at a step 408, deaerated blood exits the blood chamber, such as via tubing connected thereto. Where the blood chamber with integrated deaeration device is coupled to the outlet of a dialyzer, the blood exiting the blood chamber will be deaerated and cleansed and flow from the blood chamber into the venous bloodlines.

It should be appreciated that the system described herein could further be used for the purpose of deaerating the bloodline before blood is introduced. In this case, saline or other priming fluid would be introduced into the bloodline and then recirculated in the bloodline, during which time air in the bloodline would be passively deaerated.

Various embodiments discussed herein may be combined with each other in appropriate combinations in connection with the system described herein. Additionally, in some instances, the order of steps in the flow diagrams, flowcharts and/or described flow processing may be modified, where appropriate. Further, various aspects of the system described herein may be implemented or controlled using software, hardware, a combination of software and hardware and/or other computer-implemented or computer-controlled modules or devices having described features and performing described functions. The system may further include a display and/or other computer components for providing a suitable interface with a user and/or with other computers.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An extracorporeal blood circuit device, comprising:
   a blood chamber;
   a deaeration device integrated with the blood chamber for allowing air released from blood flowing in the blood chamber to exit the blood chamber;
   a sensor for measuring a blood constituent level, wherein the sensor performs measurements on blood in the blood chamber while the deaeration device allows air released from the blood flowing in the blood chamber to exit the blood chamber; and
   a flow diverter disposed in the blood chamber and configured to divert blood flow to enable deaeration of the blood flowing in the blood chamber while the blood constituent level in the blood in the blood chamber is measured by the sensor.

2. The extracorporeal blood circuit device according to claim 1, wherein the deaeration device comprises a vent assembly integrated with a side of the blood chamber.

3. The extracorporeal blood circuit device according to claim 2, wherein the vent assembly comprises a micro-porous membrane and a vent structure.

4. The extracorporeal blood circuit device according to claim 3, wherein the vent structure comprises a first porous layer and a second porous layer including a porous material capable of swelling when moistened, and wherein the first porous layer is disposed between the micro-porous membrane and the second porous layer and the first porous layer is less responsive to the presence of moisture than the second porous layer.

5. The extracorporeal blood circuit device according to claim 1, wherein the blood chamber is an optical blood chamber and the sensor includes an optical measurement sensor.

6. The extracorporeal blood circuit device according to claim 5, wherein the blood constituent level measured by the optical measurement sensor enables determination of a hematocrit level in the blood.

7. The extracorporeal blood circuit device according to claim 5, wherein the blood constituent level measured by the optical measurement sensor enables determination of oxygen saturation in the blood.

8. The extracorporeal blood circuit device according to claim 1, wherein the deaeration device passively removes air from the blood in the blood chamber while the sensor actively performs measurements on the blood in the blood chamber.

9. The extracorporeal blood circuit according to claim 1, wherein the flow diverter is disposed upstream of the sensor.

10. The extracorporeal blood circuit of claim 1, wherein the flow diverter is configured to guide a first portion of blood in a first direction and to guide a second portion of blood in a second direction, the first portion of blood being larger than the second portion of blood.

11. A dialysis system, comprising:
    a dialyzer; and
    an extracorporeal blood circuit device disposed adjacent to the dialyzer, the extracorporeal blood circuit device comprising:
      a blood chamber; and
      a deaeration device integrated with the blood chamber for allowing air released from blood flowing in the blood chamber to exit the blood chamber,
      a sensor for measuring a blood constituent level, and
      a flow diverter disposed in the blood chamber and configured to divert blood flow to enable deaeration of the blood flowing in the blood chamber while the blood constituent level in the blood in the blood chamber is measured by the sensor.

12. The dialysis system according to claim 11, wherein the sensor of the extracorporeal blood circuit device performs measurements on blood flowing within the blood chamber while the deaeration device allows air released from the blood flowing in the blood chamber to exit the blood chamber.

13. The dialysis system according to claim 12, wherein the blood chamber is an optical blood chamber and the sensor includes an optical measurement sensor.

14. The dialysis system according to claim 13, wherein the blood constituent level measured by the optical measurement sensor enables determination of a hematocrit level in the blood.

15. The dialysis system according to claim 11, wherein the blood chamber is configured as an S-shaped tubing coupled to the dialyzer.

16. The dialysis system according to claim 11, wherein the extracorporeal blood circuit device is coupled to an outlet of the dialyzer.

17. The dialysis system according to claim 11, wherein the extracorporeal blood circuit device is coupled to an inlet of the dialyzer.

18. The dialysis system according to claim 11, wherein the extracorporeal blood circuit device is a first extracorporeal blood circuit device having a first blood chamber and a first deaeration device, and wherein the dialysis system further comprises a second extracorporeal blood circuit device comprising a second blood chamber and a second deaeration device integrated with the second blood chamber for removing air from blood flowing into the second blood chamber.

19. The dialysis system according to claim 18, wherein the first extracorporeal blood circuit device is coupled to an outlet of the dialyzer and further comprises a sensor for measuring a blood constituent level, wherein the sensor performs measurements on blood in the first blood chamber while the deaeration device removes air from the blood in the first blood chamber, and wherein the second extracorporeal blood circuit is coupled to an inlet of the dialyzer.

20. The dialysis system according to claim 11, wherein the deaeration device comprises a vent assembly integrated with a side of the blood chamber.

21. The dialysis system according to claim 11, wherein the flow diverter is disposed upstream of the sensor.

22. The dialysis system of claim 11, wherein the flow diverter is configured to guide a first portion of blood in a first direction and to guide a second portion of blood in a second direction, the first portion of blood being larger than the second portion of blood.

23. A method for measuring and deaerating blood in an extracorporeal blood circuit, the method comprising:
  coupling a blood chamber with an integrated deaeration device to an outlet of a dialyzer;
  passively deaerating blood flowing in the blood chamber from the dialyzer and allowing air released from the blood in the blood chamber to exit the blood chamber via the integrated deaeration device; and
  actively performing measurements on the blood in the blood chamber using a sensor associated with the blood chamber.

24. The method according to claim 23, wherein the blood chamber is an optical blood chamber and the sensor includes an optical measurement sensor, and wherein a blood constituent level measured by the optical measurement sensor enables determination of a hematocrit level in the blood.

* * * * *

UNITED STATES PATENT AND TRADEMARK OFFICE
CERTIFICATE OF CORRECTION

Page 1 of 1

PATENT NO. : 9,945,838 B2
APPLICATION NO. : 14/972769
DATED : April 17, 2018
INVENTOR(S) : Matthew Doyle It is certified that error appears in the above-identified patent and that said Letters Patent is hereby corrected as shown below:

In the Claims

Claim 1
Column 9, Line 63, delete "in the blood in the blood" and insert --in the blood--.

Claim 11
Column 10, Line 50, delete "in the blood in the blood" and insert --in the blood--.

Signed and Sealed this
Twelfth Day of March, 2019

Andrei Iancu
*Director of the United States Patent and Trademark Office*